(12) United States Patent
Murakoshi

(10) Patent No.: US 10,989,734 B2
(45) Date of Patent: Apr. 27, 2021

(54) INFORMATION PROCESSING APPARATUS, INFORMATION PROCESSING METHOD, AND STORAGE MEDIUM

(71) Applicant: SONY CORPORATION, Tokyo (JP)

(72) Inventor: Sho Murakoshi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 280 days.

(21) Appl. No.: 15/778,976

(22) PCT Filed: Nov. 22, 2016

(86) PCT No.: PCT/JP2016/084608
§ 371 (c)(1),
(2) Date: May 24, 2018

(87) PCT Pub. No.: WO2017/122430
PCT Pub. Date: Jul. 20, 2017

(65) Prior Publication Data
US 2018/0348252 A1 Dec. 6, 2018

(30) Foreign Application Priority Data

Jan. 13, 2016 (JP) .............................. JP2016-004552

(51) Int. Cl.
*G01P 21/00* (2006.01)
*A61B 5/11* (2006.01)
(Continued)

(52) U.S. Cl.
CPC .............. *G01P 21/00* (2013.01); *A61B 5/11* (2013.01); *A61B 5/1117* (2013.01); *A61B 5/22* (2013.01);
(Continued)

(58) Field of Classification Search
CPC ........ G01P 15/00; G01P 21/00; A61B 5/7214; A61B 5/1117; A61B 5/7246; A61B 5/22;
(Continued)

(56) References Cited

U.S. PATENT DOCUMENTS 4,667,114 A     5/1987  Rossi
5,671,981 A  *  9/1997  Sasaki ..................... B60T 8/885
                                                 303/122.06
(Continued)

FOREIGN PATENT DOCUMENTS

EP       1818016 A1     8/2007
JP     H08-292112 A    11/1996
(Continued)

OTHER PUBLICATIONS

English translation of prior art document Masahiko et al. JP 2008-247145 filed May 24, 2018 (Year: 2008).*

*Primary Examiner* — Herbert K Roberts
*Assistant Examiner* — John M Royston
(74) *Attorney, Agent, or Firm* — Paratus Law Group, PLLC

(57) ABSTRACT

There is provided an information processing apparatus to provide a mechanism capable of improving accuracy of detection of abnormality of sensors without changing configurations of the sensors, the information processing apparatus including: an acquisition unit configured to obtain a first value obtained by measurement in a first measurement unit and a second value obtained by measurement in a second measurement unit whose dynamic range regarding measurement is a second dynamic range different from a first dynamic range of the first measurement unit; and a detection unit configured to detect abnormality of the first value or the second value on a basis of a change in a correlation between the first value and the second value.

13 Claims, 13 Drawing Sheets

(51) Int. Cl.
   *G01P 15/00*   (2006.01)
   *A63B 69/36*   (2006.01)
   *A61B 5/22*    (2006.01)
   *A61B 5/00*    (2006.01)
   *G01P 15/08*   (2006.01)
   *A63B 53/00*   (2015.01)
   *A63B 102/32*  (2015.01)
   *A63B 53/04*   (2015.01)

(52) U.S. Cl.
   CPC .......... *A61B 5/7214* (2013.01); *A61B 5/7246* (2013.01); *A63B 53/00* (2013.01); *A63B 69/36* (2013.01); *A63B 69/3632* (2013.01); *G01P 15/00* (2013.01); *G01P 15/0802* (2013.01); *A61B 5/1121* (2013.01); *A61B 2562/0219* (2013.01); *A61B 2562/04* (2013.01); *A63B 53/04* (2013.01); *A63B 2102/32* (2015.10); *A63B 2220/40* (2013.01); *A63B 2220/833* (2013.01); *A63B 2225/02* (2013.01)

(58) Field of Classification Search
   CPC ..... A61B 5/11; A61B 5/1121; A61B 2562/04; A61B 2562/0219; A63B 69/36; A63B 53/00; A63B 69/3632; A63B 2225/02; A63B 2220/833; A63B 2220/40; A63B 53/04; A63B 2102/32
   See application file for complete search history.

(56) References Cited

U.S. PATENT DOCUMENTS

| | | | |
|---|---|---|---|
| 5,868,423 A * | 2/1999 | Takimoto | B60R 21/01546 280/735 |
| 7,996,158 B2 * | 8/2011 | Hayter | A61B 5/14532 600/345 |
| 2002/0024254 A1 | 2/2002 | Marlett et al. | |
| 2013/0185003 A1 * | 7/2013 | Carbeck | A61B 5/1036 702/41 |
| 2015/0282768 A1 | 10/2015 | Luna et al. | |

FOREIGN PATENT DOCUMENTS

| | | |
|---|---|---|
| JP | 2008-247145 A | 10/2008 |
| JP | 4667114 B2 | 4/2011 |
| JP | 2014-183931 A | 10/2014 |
| WO | WO 2014/110190 A2 | 7/2014 |

\* cited by examiner

INFORMATION PROCESSING APPARATUS, INFORMATION PROCESSING METHOD, AND STORAGE MEDIUM

CROSS REFERENCE TO PRIOR APPLICATION

This application is a National Stage Patent Application of PCT International Patent Application No. PCT/JP2016/084608 (filed on Nov. 22, 2016) under 35 U.S.C. § 371, which claims priority to Japanese Patent Application No. 2016-004552 (filed on Jan. 13, 2016), which are all hereby incorporated by reference in their entirety.

TECHNICAL FIELD

The present disclosure relates to an information processing apparatus, an information processing method, and a storage medium.

BACKGROUND ART

Utilization of information obtained by measurement in a sensor (hereinafter, also referred to as "measurement information") has been increased in accordance with development of a sensor technology. For example, in the field of sport, there exists a technology of causing a player to wear a sensor such as a motion sensor to determine movement of the player on the basis of measurement information obtained from the motion sensor.

Herein, a measurable range of the sensor is generally limited in accordance with specifications of the sensor and the like. Specifically, the measurable range of the sensor has an upper limit and a lower limit, and, in a case where a degree of a phenomenon serving as a target to be measured exceeds the upper limit or lower limit of the measurable range, it is difficult to obtain accurate measurement information. Therefore, measurable movements are increased as the measurable range is wider. On the contrary, measurable movements are reduced as the measurable range is narrower. An index that indicates an extent of the measurable range is a dynamic range.

Meanwhile, the extent of the measurable range and measurable accuracy have a trade-off relationship in many cases. For example, resolution of the measurement information is lower as the dynamic range is higher, and variations in the measurement information tend to be large. On the contrary, the resolution of the measurement information is higher as the dynamic range is lower, and variations in the measurement information tend to be small.

In view of this, there is proposed a technology of using two sensors having different extents of a measurable range, i.e., resolutions of measurement information. For example, Patent Literature 1 discloses an information processing apparatus that acquires time-series measurement information from a shock sensor and a motion sensor having higher resolution than that of the shock sensor and sets an analysis target section regarding the time-series measurement information of the motion sensor on the basis of the measurement information of the shock sensor. According to the disclosure, Patent Literature 1 describes that the analysis target section is appropriately set and determination accuracy of a motion pattern is improved.

CITATION LIST

Patent Literature

Patent Literature 1: JP 2014-183931A

DISCLOSURE OF INVENTION

Technical Problem

However, a case where abnormality occurs in any one of the two sensors is not considered in the disclosure of Patent Literature 1 cited above. Further, it is desired to accurately detect abnormality of the sensor in terms of efficiency of coping with abnormality of the sensor. Furthermore, it is difficult to change configurations of the sensors in some cases. Therefore, there has been demanded a mechanism capable of improving accuracy of detection of abnormality of sensors without changing configurations of the sensors.

Solution to Problem

According to the present disclosure, there is provided an information processing apparatus including: an acquisition unit configured to obtain a first value obtained by measurement in a first measurement unit and a second value obtained by measurement in a second measurement unit whose dynamic range regarding measurement is a second dynamic range different from a first dynamic range of the first measurement unit; and a detection unit configured to detect abnormality of the first value or the second value on a basis of a change in a correlation between the first value and the second value.

In addition, according to the present disclosure, there is provided an information processing method including: obtaining, by a processor, a first value obtained by measurement in a first measurement unit and a second value obtained by measurement in a second measurement unit whose dynamic range regarding measurement is a second dynamic range different from a first dynamic range of the first measurement unit; and detecting abnormality of the first value or the second value on a basis of a change in a correlation between the first value and the second value.

In addition, according to the present disclosure, there is provided a storage medium storing a program for causing a computer to achieve: an acquisition function of obtaining a first value obtained by measurement in a first measurement unit and a second value obtained by measurement in a second measurement unit whose dynamic range regarding measurement is a second dynamic range different from a first dynamic range of the first measurement unit; and a detection function of detecting abnormality of the first value or the second value on a basis of a change in a correlation between the first value and the second value.

Advantageous Effects of Invention

According to the present disclosure as described above, there is provided a mechanism capable of improving accuracy of detection of abnormality of sensors without changing configurations of the sensors. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
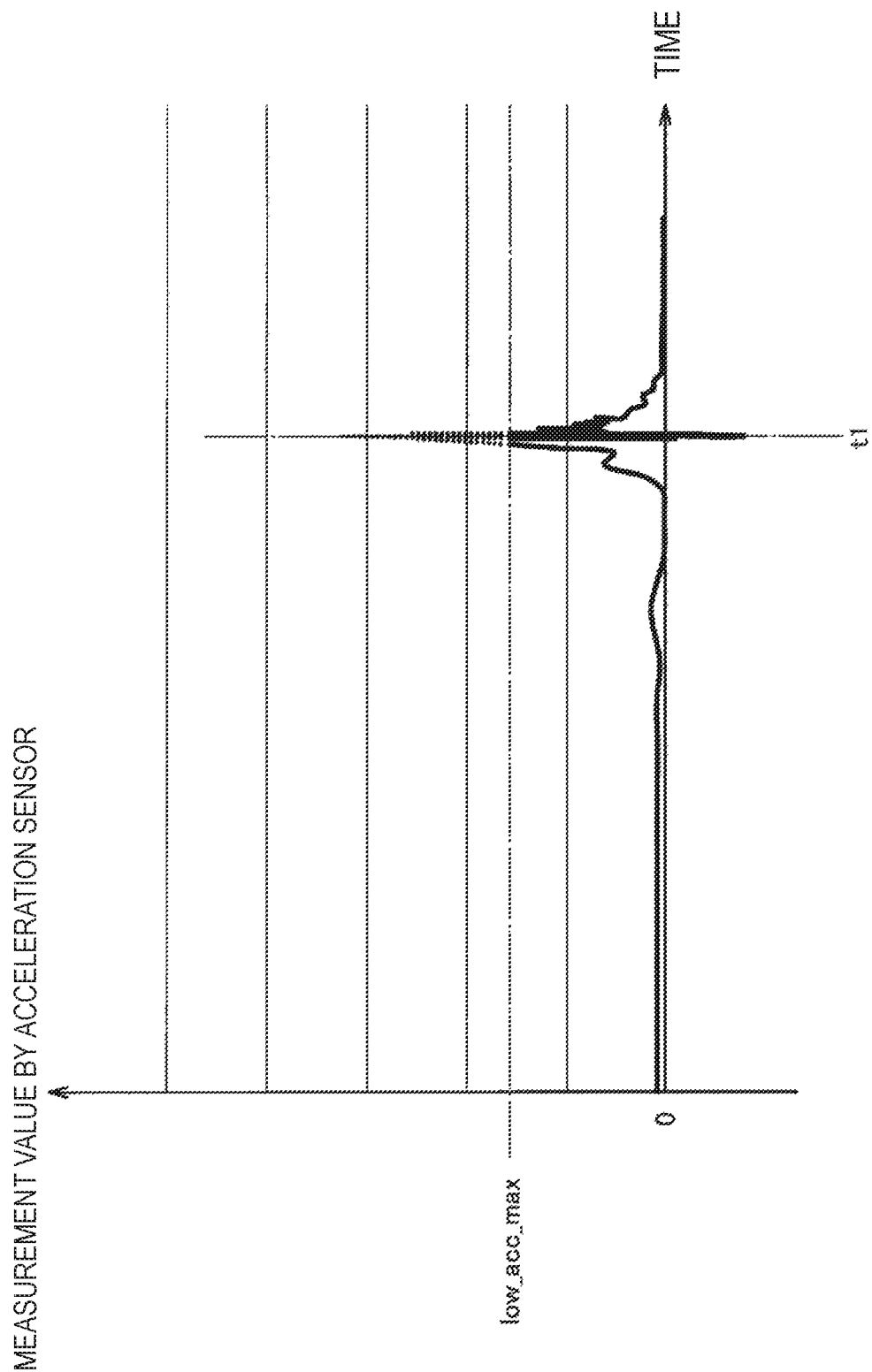
FIG. 1 is a graph showing an example of measurement results of acceleration sensors in an information processing system according to a first embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, in the present specification and drawings, a plurality of constituent members having substantially the same functional configuration are distinguished by adding different numbers to the same reference sign in some cases. For example, a plurality of configurations having substantially the same function are distinguished as necessary, such as "first acceleration sensor 200A" and "second acceleration sensor 200B". However, in a case where it is unnecessary to distinguish substantially the same functional configurations, the same functional configurations are denoted only by the same reference sign. For example, in a case where it is unnecessary to distinguish between the first acceleration sensor 200A and the second acceleration sensor 200B in particular, those acceleration sensors are simply referred as acceleration sensors 200.

Note that description will be provided in the following order.

1. First embodiment (example of acceleration sensor)
1-1. Overview
1-2. Configuration of apparatus
1-3. Processing of apparatus
1-4. Conclusion of first embodiment
2. Second embodiment (example of angular velocity sensor)
2-1. Overview
2-2. Configuration of apparatus
2-3. Processing of apparatus
2-4. Conclusion of second embodiment
3. Conclusion

1. First Embodiment (Example of Acceleration Sensor)

First, a first embodiment of the present disclosure will be described. In the first embodiment, there will be described a mechanism that detects abnormality occurring in a sensor and notifies a user of the abnormality by using acceleration sensors as an example.

<1-1. Overview>

First, an overview of an information processing system serving as the mechanism according to the present embodiment will be described. The information processing system includes two sensors and an information processing apparatus. Each of the sensors measures presence/absence of a predetermined phenomenon or a degree thereof and generates measurement information based on a measurement result. For example, the measurement information is a time-series measurement value. Further, the information processing apparatus has a measurement information acquisition function and a measurement information processing function. The measurement information acquisition function acquires measurement information from the sensor. The measurement information processing function performs processing such as generation of new measurement information or analysis of a change in the measurement information or a pattern thereof (pattern matching) on the basis of the measurement information. Further, the overview of the information processing system will be described in detail with reference to FIG. 1. FIG. 1 is a graph showing an example of measurement results of acceleration sensors 200 in the information processing system according to the present embodiment.

For example, the information processing system includes a first acceleration sensor 200A serving as a first measurement unit and a second acceleration sensor 200B serving as a second measurement unit, which are two acceleration sensors having different dynamic ranges, and an information processing apparatus 100-1. Each of the acceleration sensors 200 measures acceleration and generates measurement information including a measurement value indicating the measured acceleration. The information processing apparatus 100-1 acquires pieces of measurement information from the respective acceleration sensors 200 and combines the pieces of measurement information, thereby generating new measurement information. For example, the information processing apparatus 100-1 generates new measurement information that is a measurement value of the second acceleration sensor 200B within a measurable range of the second acceleration sensor 200B (hereinafter, also referred to as "second measurable range") whose dynamic range is lower than that of the first acceleration sensor 200A and is a measurement value of the first acceleration sensor 200A out of the second measurable range. When referring to FIG. 1, in a case where the generated acceleration is less than low_acc_max that is an upper limit of the second measurable range, the measurement value of the second acceleration sensor 200B (solid line) is used, and, in a case where the generated acceleration is equal to or larger than the low_acc_max, the measurement value of the first acceleration sensor 200A (dotted line) is used. This is to cover measurement information out of the second measurable range while using measurement information of the second acceleration sensor 200B having relatively high resolution. The second acceleration sensor 200B whose dynamic range is relatively lower than that of the first acceleration sensor 200A has high resolution but has a small measurable range, and therefore there is a high possibility that the generated acceleration exceeds the measurable range. In view of this, regarding acceleration out of the second measurable range, measurement information of the first acceleration sensor 200A having a relatively high dynamic range is used.

The information processing system including those sensors is used to, for example, detect a movement of the user. For example, the sensors are caused to be mounted on a player of sport as described above, and a movement of the player is analyzed on the basis of measurement information obtained from the sensors.

Herein, a shock is generated by a movement of the user in some cases. For example, in a case where the acceleration sensor 200 is attached to a head portion of a golf club and a ball is hit by using the golf club, a shock is generated when the ball is hit on the golf club. The shock appears as a change in acceleration sharper than acceleration during a swing. When referring to FIG. 1, the measurement value of the acceleration sensor 200 is sharply changed in a short time in the vicinity of a time t1 in FIG. 1, and therefore it is considered that a shock is generated in the vicinity of the time t1.

Figure 2:
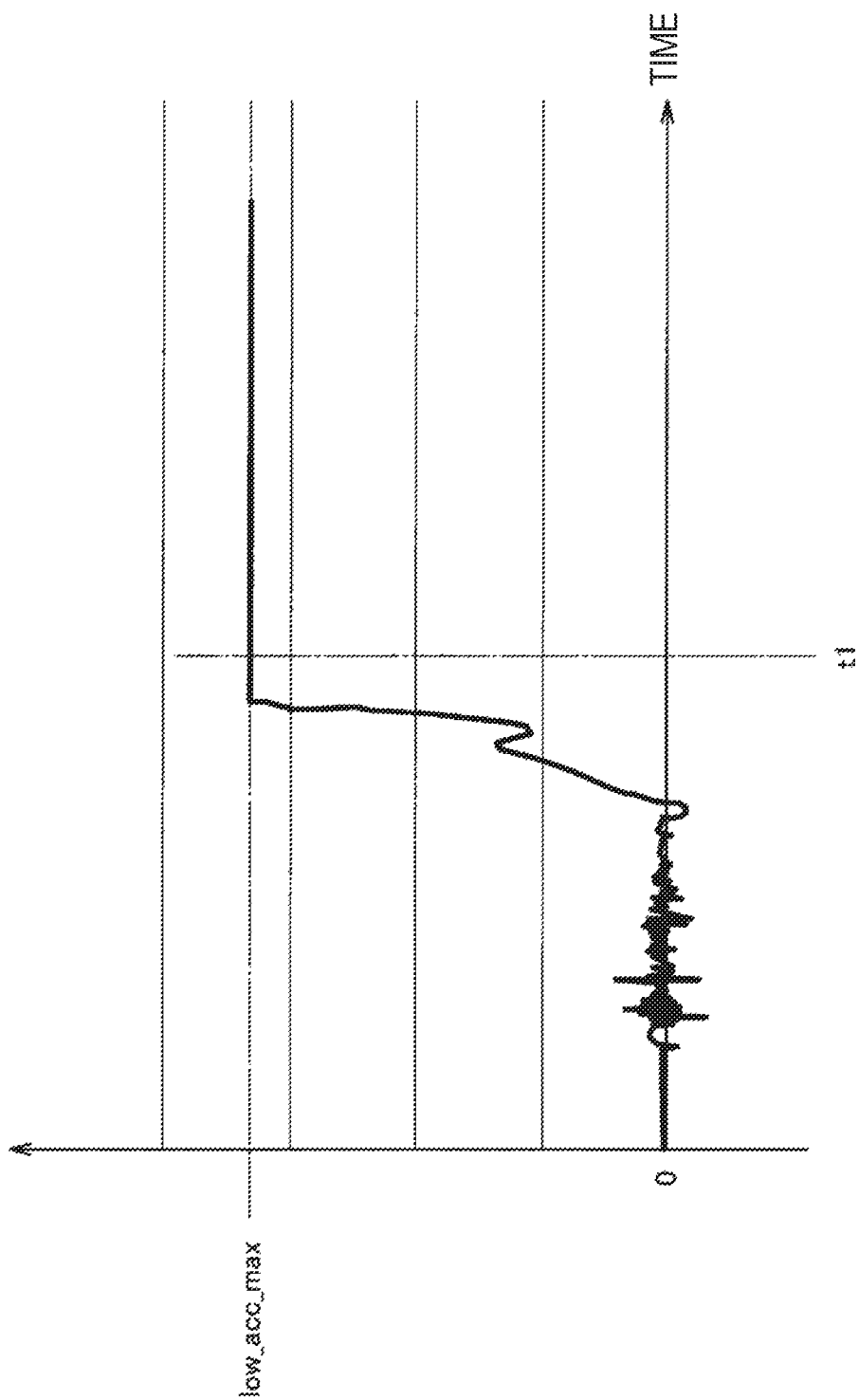
FIG. 2 is a graph showing an example of a sticking phenomenon of a measurement value of a second acceleration sensor caused by a shock generated in the vicinity of a time t1 in FIG. 1.

In such a case, abnormality of the sensor occurs due to the shock in some cases. Specifically, measurement information of the second acceleration sensor 200B having a relatively low dynamic range is fixed to a position in the vicinity of the upper limit or lower limit of the second measurable range after the shock is generated (Hereinafter, "being fixed to values in the vicinity of a certain value" will also be referred to as "sticking"), and sticking of the measurement information continues after the shock ends in some cases. Note that "vicinity" herein means a range of variations in values based on a specified value. Further, a sticking phenomenon of the acceleration sensor 200 caused by the shock will be described in detail with reference to FIG. 2. FIG. 2 is a graph showing an example of the sticking phenomenon of the measurement value of the second acceleration sensor 200B caused by the shock generated in the vicinity of the time t11 in FIG. 1.

First, a case where no abnormality occurs in the sensor will be described. For example, the measurement value of the second acceleration sensor 200B is sharply increased in response to generation of the shock, reaches the low_acc_max, and then sticks to the low_acc_max while the shock continues, i.e., while acceleration is being equal to or more than the low_acc_max. Then, when the shock ends and the acceleration is reduced to be less than the low_acc_max, the measurement value of the second acceleration sensor 200B starts to be changed again in accordance with the acceleration. This is a phenomenon that is generated because the dynamic range of the second acceleration sensor 200B is low, and therefore, generally, this phenomenon is not considered to be abnormality of the sensor.

On the contrary, in a case where abnormality occurs in the sensor, abnormality also occurs in measurement information. For example, the measurement value of the second acceleration sensor 200B reaches the low_acc_max and sticks in the vicinity of the low_acc_max while the shock continues as in the above description, but, in a case where abnormality occurs in the sensor, the sticking phenomenon of the measurement value continues even though the shock ends in some cases as illustrated in FIG. 2.

In this case, the measurement value of the second acceleration sensor 200B cannot be used, and therefore the measurement value of the first acceleration sensor 200A is used instead in many cases. However, resolution of the first acceleration sensor 200A is lower than that of the second acceleration sensor 200B, and therefore accuracy of the measurement value is reduced. Thus, it may be difficult to obtain a desired result in processing based on the measurement value. Accordingly, it is desirable to solve or restrain abnormality of the second acceleration sensor 200B.

Figure 3:
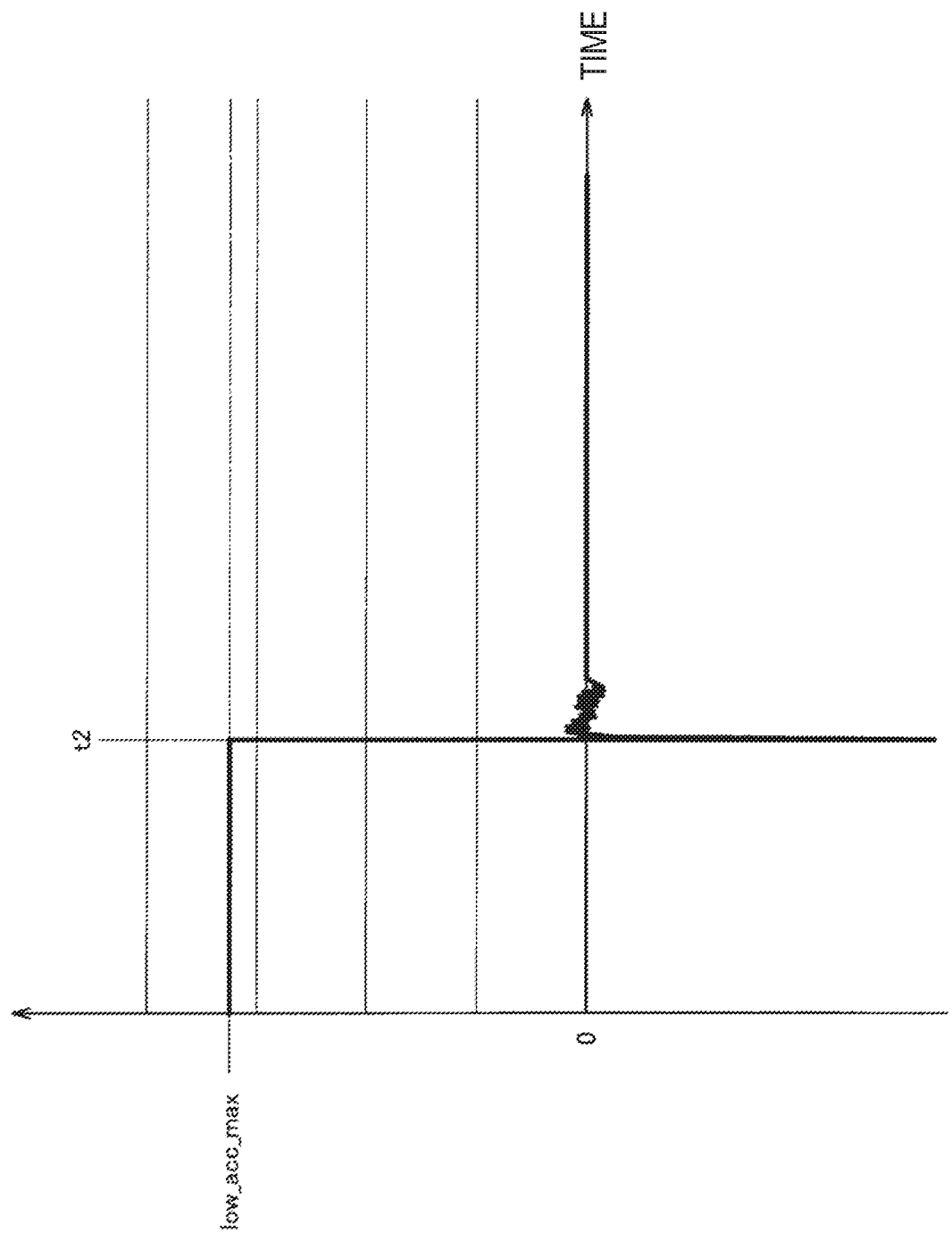
FIG. 3 is a graph showing an example of a state in which sticking of a measurement value of a second acceleration sensor is solved.

Meanwhile, it is difficult to solve such abnormality of the sensor in the apparatus or sensor in some cases. One reason of this is existence of abnormality of the sensor that is solved when a shock is applied again. For example, it is found that the above-mentioned abnormality of the second acceleration sensor 200B, i.e., sticking of the measurement value in the vicinity of the upper limit of the second measurable range is solved when a shock is applied to the second acceleration sensor 200B again. Solution of the sticking phenomenon of the acceleration sensor 200 by applying a shock again will be described in detail with reference to FIG. 3. FIG. 3 is a graph showing an example of a state in which sticking of the measurement value of the second acceleration sensor 200B is solved.

After the measurement value of the second acceleration sensor 200B sticks as illustrated in FIG. 2, sticking of the measurement value continues in FIG. 3. Thereafter, when a shock is applied to the second acceleration sensor 200B again at a time t2, the sticking of the measurement value is solved and the measurement value starts to be changed in accordance with generated acceleration.

However, it is generally difficult to cause the shock to be generated in the apparatus or sensor. Therefore, the information processing apparatus 100-1 or the like prompts the user to generate a shock again. Meanwhile, a burden on the user is increased because the user is caused to perform operation for generating a shock. Therefore, the burden on the user is expected to be reduced as much as possible.

Further, it is also difficult to restrain abnormality of a sensor main body in some cases. This is because, as one reason, it is difficult to specify a cause of abnormality. For example, in a case where the sensor is a ready-made product, it is generally impossible to sufficiently grasp a mechanism or structure of the sensor, and thus it is difficult to specify a cause of abnormality. Therefore, it is also difficult to add a configuration for restraining abnormality of the sensor in advance.

In view of this, the present embodiment proposes an information processing system capable of improving accuracy of detecting abnormality of sensors without changing configurations of the sensors. Hereinafter, constituent members of the information processing system will be described in detail. Note that, for convenience of explanation, information processing apparatuses 100 according to the first and second embodiments are distinguished by adding numbers corresponding to the embodiments to the end, such as "information processing apparatus 100-1" and "information processing apparatus 100-2".

<1-2. Configuration of Apparatus>

Next, there will be described a configuration of the information processing apparatus 100-1 that is a main constituent member of the information processing system according to the present embodiment.

(Physical Configuration of Information Processing Apparatus)

Figure 4:
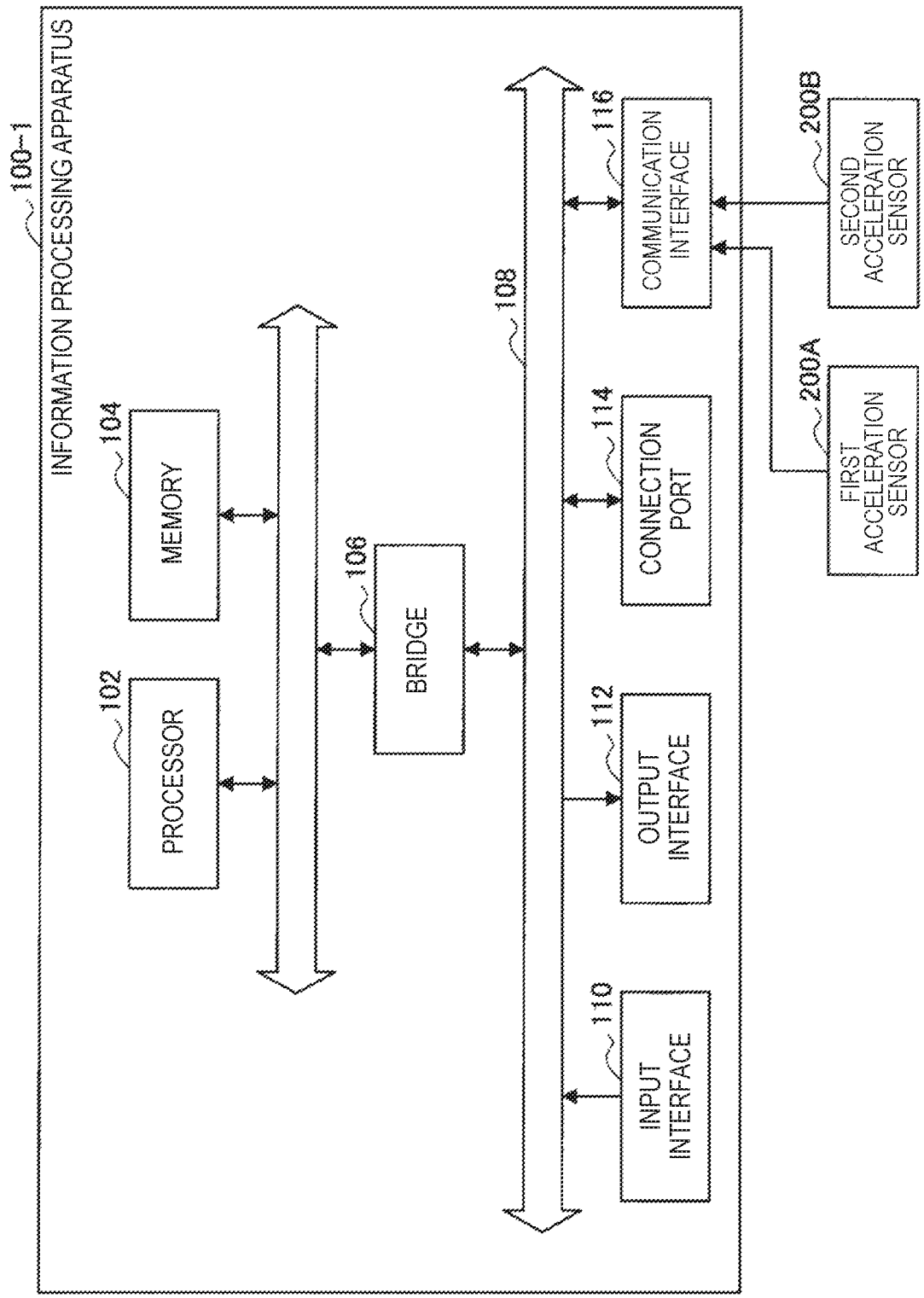
FIG. 4 is a block diagram illustrating a schematic physical configuration example of an information processing apparatus according to this embodiment.

First, a physical configuration of the information processing apparatus 100-1 will be described with reference to FIG. 4. FIG. 4 is a block diagram illustrating a schematic physical configuration example of the information processing apparatus 100-1 according to the present embodiment.

As illustrated in FIG. 4, the information processing apparatus 100-1 includes a processor 102, a memory 104, a bridge 106, a bus 108, an input interface 110, an output interface 112, a connection port 114, and a communication interface 116.

(Processor)

The processor 102 is a control module that functions as an arithmetic processing unit and achieves functions of a detection unit 122 and a display control unit 126 described below in the information processing apparatus 100-1 in cooperation with various kinds of programs. The processor 102 executes a program stored on the memory 104 or another storage medium by using a control circuit, thereby achieving various logical functions of the information processing apparatus 100-1 described below. For example, the processor 102 can be a central processing unit (CPU), a graphics processing unit (GPU), a digital signal processor (DSP), or a system-on-a-chip (SoC).

(Memory)

The memory 104 stores programs, operation parameters, or the like used by the processor 102 and achieves a function of a storage unit 124 described below. For example, the memory 104 includes a random access memory (RAM) and temporarily stores programs used in execution of the processor 102, parameters that are appropriately changed in execution, or the like. Further, the memory 104 includes a read only memory (ROM). Note that an external storage device may be used as part of the memory 104 via a connection port, a communication apparatus, or the like.

Note that the processor 102 and the memory 104 are connected to each other via an internal bus made up of a CPU bus or the like.

(Bridge and Bus)

The bridge 106 connects buses. Specifically, the bridge 106 connects an internal bus to which the processor 102 and the memory 104 are connected and the bus 108 that connects the input interface 110, the output interface 112, the connection port 114, and the communication interface 116.

(Input Interface)

The input interface 110 is used to allow the user to operate the information processing apparatus 100-1 or input information to the information processing apparatus 100-1. For example, the input interface 110 is made up of input means for allowing the user to input information such as a button for starting the information processing apparatus 100-1, an input control circuit that generates an input signal on the basis of input from the user and outputs the input signal to the processor 102, and the like. Note that the input means may be a mouse, a keyboard, a touchscreen, a switch, a lever, or the like. By operating the input interface 110, the user of the information processing apparatus 100-1 can input various kinds of data to the information processing apparatus 100-1 and instruct the information processing apparatus 100-1 to execute processing.

(Output Interface)

The output interface 112 is used to notify the user of information. For example, the output interface 112 performs output to an apparatus such as a liquid crystal display (LCD) device, an organic light emitting diode (OLED) device, or a projector, thereby achieving a function of a display unit 128 described below. Note that the output interface 112 may perform output to an apparatus such as a speaker or headphones.

(Connection Port)

The connection port 114 is a port for directly connecting a device to the information processing apparatus 100-1. For example, the connection port 114 can be a universal serial bus (USB) port, an IEEE1394 port, a small computer system interface (SCSI) port, or the like. Further, the connection port 114 may be an RS-232C port, an optical audio terminal, a high-definition multimedia interface (HDMI) (registered trademark) port, or the like. By connecting an external device to the connection port 114, data may be exchanged between the information processing apparatus 100-1 and the device.

(Communication Interface)

The communication interface 116 mediates communication between the information processing apparatus 100-1 and an external device and achieves a function of a communication unit 120 described below. For example, the communication interface 116 executes wireless communication in accordance with an arbitrary wireless communication method including a short-range wireless communication method such as Bluetooth (registered trademark), near field communication (NFC), wireless USB, and TransferJet (registered trademark), a cellular communication method such as wideband code division multiple access (WCDMA) (registered trademark), WiMAX (registered trademark), long term evolution (LTE), and LTE-A, and a wireless local area network (LAN) method such as Wi-Fi (registered trademark). Further, the communication interface 116 may execute wired communication that is communication performed with a wire.

Note that the information processing apparatus 100-1 may not have part of the configuration described with reference to FIG. 4 and may have an additional configuration. Further, a one-chip information processing module in which the whole or part of the configuration described with reference to FIG. 4 is integrated may be provided.

(Logical Configuration of Information Processing Apparatus)

Figure 5:
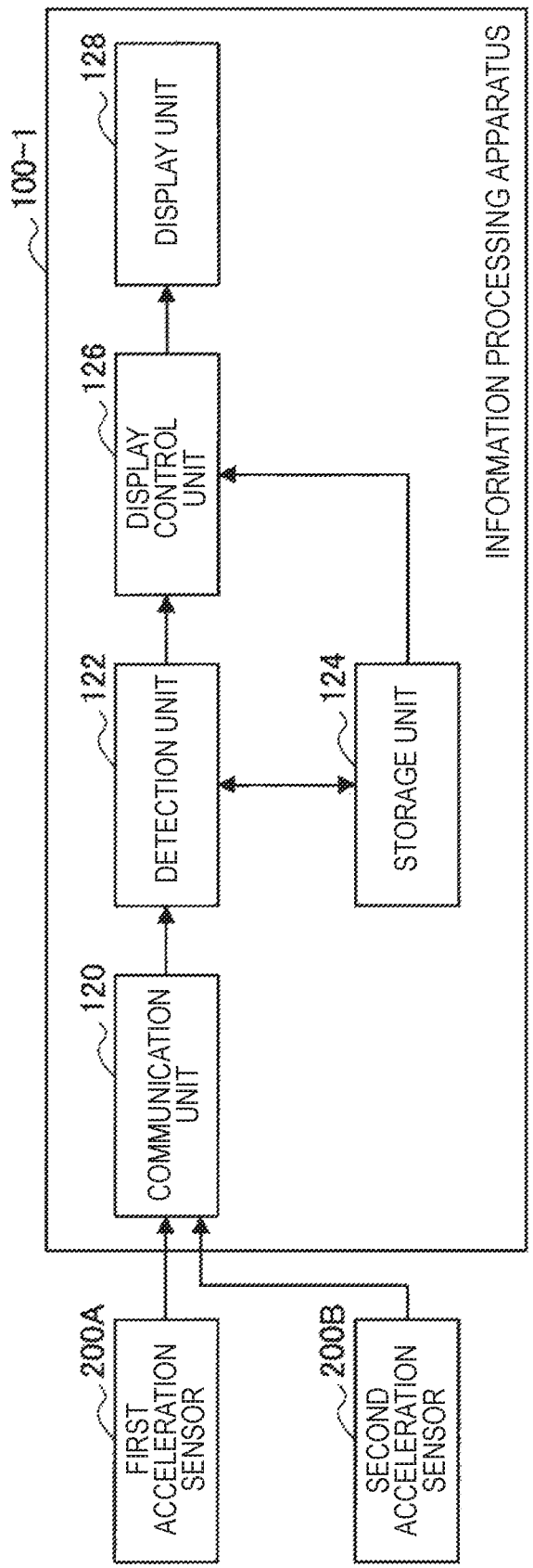
FIG. 5 is a block diagram illustrating a schematic functional configuration example of the information processing apparatus according to this embodiment.

Next, a logical configuration of the information processing apparatus 100-1 according to the present embodiment will be described with reference to FIG. 5. FIG. 5 is a block diagram illustrating a schematic functional configuration example of the information processing apparatus 100-1 according to the present embodiment.

As illustrated in FIG. 5, the information processing apparatus 100-1 includes the communication unit 120, the detection unit 122, the storage unit 124, the display control unit 126, and the display unit 128.

(Communication Unit)

The communication unit 120 communicates with the acceleration sensors 200. Specifically, the communication unit 120 receives measurement information from each of the first and second acceleration sensors 200A and 200B. For example, the communication unit 120 communicates with the acceleration sensors 200 by using a wireless communication method. Note that the communication unit 120 may communicate with the acceleration sensors 200 by using a wired communication method. Further, the received measurement information may be time-series measurement information or may be a single piece of measurement information.

(Detection Unit)

Figure 6:
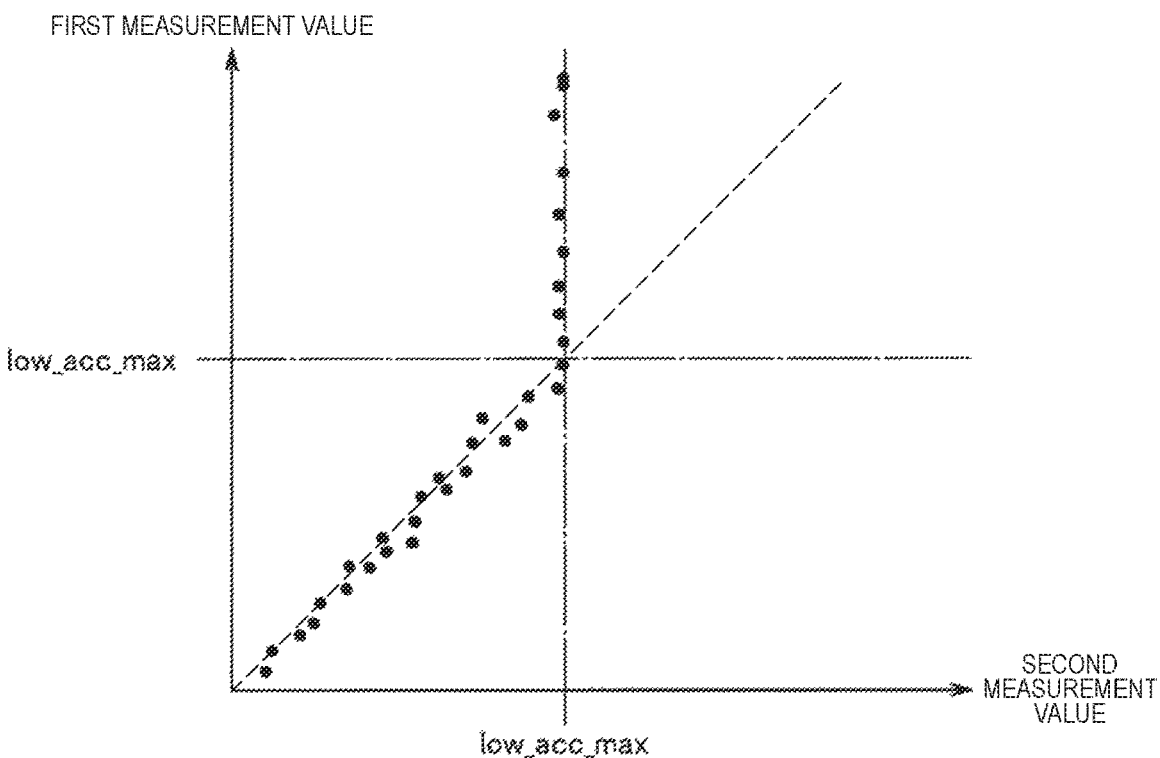
FIG. 6 is a graph showing an example of a correlation between a first measurement value and a second measurement value obtained in a case where no abnormality occurs in an acceleration sensor.
Figure 7:
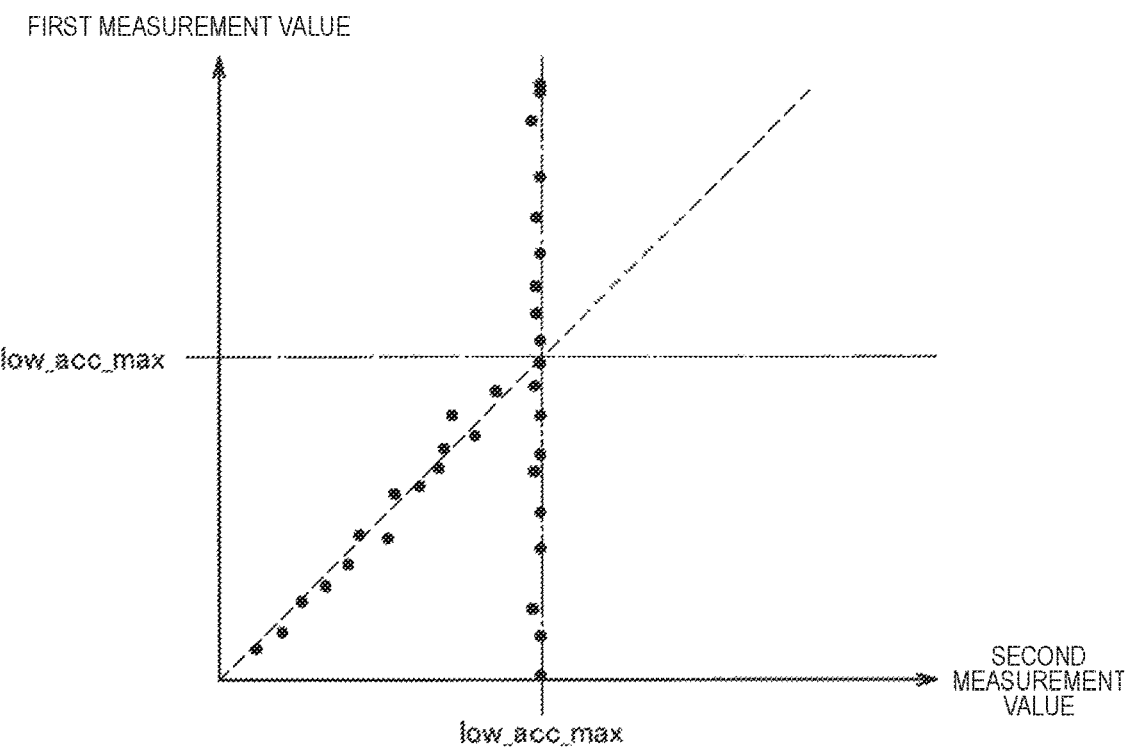
FIG. 7 is a graph showing an example of a correlation between a first measurement value and a second measurement value obtained in a case where abnormality occurs in an acceleration sensor.

The detection unit 122 detects abnormality of the measurement information received from the acceleration sensor 200 (i.e., abnormality of the acceleration sensor 200). Specifically, the detection unit 122 detects abnormality of the measurement information on the basis of a change in a correlation between measurement information obtained by measurement in the first acceleration sensor 200A serving as a first value (hereinafter, also referred to as "first measurement information" or "first measurement value") and measurement information obtained by measurement in the second acceleration sensor 200B serving as a second value (hereinafter, also referred to as "second measurement information" or "second measurement value"). Further, the detection unit 122 performs detection processing in response to generation of a shock. Note that, as described above, a dynamic range regarding measurement in the first acceleration sensor 200A (hereinafter, also referred to as "first dynamic range") is different from a dynamic range regarding measurement in the second acceleration sensor 200B (hereinafter, also referred to as "second dynamic range"). Specifically, the first dynamic range is higher than the second dynamic range. Further, hereinafter, in a case where the first measurement value and the second measurement value are not distinguished, those measurement values will also be simply referred to as "measurement values". Furthermore, processing of the detection unit 122 will be described in detail with reference to FIGS. 6 and 7. FIG. 6 is a graph showing an example of the correlation between the first measurement value and the second measurement value obtained in a case where no abnormality occurs in the acceleration sensor 200, and FIG. 7 is a graph showing an example of the correlation between the first measurement value and the second measurement value obtained in a case where abnormality occurs in the acceleration sensor 200.

First, the detection unit 122 determines whether or not a shock has been generated on the basis of measurement information. For example, in a case where an inclination of a change in a measurement value in the vicinity of the time t1 illustrated in FIG. 1 is equal to or larger than a threshold, the detection unit 122 determines that a shock has been generated. Further, the detection unit 122 may determine whether or not a shock has been generated on the basis of the correlation between the first and second measurement values. For example, in a case where the first measurement value of the first acceleration sensor falls within a range including values higher than the low_acc_max in a state in which the second measurement value of the second acceleration sensor having a low dynamic range sticks to the low_acc_max that is the upper limit of the second measurable range as illustrated in FIG. 6, the detection unit 122 may determine that a shock has been generated. Note that a period of time in which the first measurement value falls within the range including values higher than the low_acc_max in a state in which the second measurement value sticks to the low_acc_max may be estimated as a period of time in which a shock is generated.

In a case where it is determined that a shock has been generated, the detection unit 122 specifies the correlation on the basis of the acquired measurement information. Specifically, the detection unit 122 specifies the correlation before the shock and the correlation after the shock on the basis of the measurement information. For example, the detection unit 122 may calculate an index such as a correlation coefficient (correlation function) in a predetermined period of time before the shock is generated and an index in a predetermined period of time after the shock ends. Note that the indexes are not limited to correlation coefficients, and any index can be employed as long as the index is information with which a correlation of data can be grasped.

Next, the detection unit 122 determines whether or not the correlation after the shock ends has been changed from the correlation before the shock is generated. Specifically, the detection unit 122 determines presence/absence of the correlation before the first measurement value exceeds the second measurable range and the correlation after the first measurement value falls within the second measurable range again or determines a change in a degree of the correlation. For example, the detection unit 122 determines whether or not the correlation coefficient before the shock is generated matches with the correlation coefficient after the shock ends or whether or not those correlation coefficients fall within a predetermined range.

Specifically, as illustrated in FIGS. 6 and 7, first, both in a case where no abnormality occurs in the sensor and in a case where abnormality occurs in the sensor, the correlation in a predetermined period of time before the shock is generated, i.e., before the first measurement value exceeds the low_acc_max has a nearly linear relationship (broken line). Therefore, a positive correlation coefficient is calculated in this period of time.

Further, the generated acceleration exceeds the measurable range of the second acceleration sensor 200B while the shock is being generated, i.e., while the first measurement value is exceeding the low_acc_max, and therefore the second measurement value sticks to the low_acc_max. Therefore, there is no correlation in this period of time, and a calculated correlation coefficient is 0 or a value close to 0.

Further, in a case where no abnormality occurs in the sensor after the first measurement value becomes less than the low_acc_max again, the correlation has a nearly linear relationship that is the same as the relationship before the first measurement value exceeds the low_acc_max as illustrated in FIG. 6. Therefore, a positive correlation coefficient is calculated in this period of time. Meanwhile, in FIG. 7, although the first measurement value becomes less than the low_acc_max again, the second measurement value sticks in the vicinity of the low_acc_max. Therefore, in this period of time, as well as in the period in which the shock is generated, there is no correlation and a correlation coefficient of 0 or close to 0 is calculated.

Therefore, the detection unit 122 determines that the correlation coefficients match in a case of FIG. 6 and determines that the correlation coefficients do not match in a case of FIG. 7.

Then, in a case where it is determined that the correlation after the shock ends has been changed from the correlation before the shock is generated, the detection unit 122 detects abnormality of the sensor. For example, in a case where the calculated correlation coefficients match, the detection unit 122 does not detect abnormality of the sensor. On the contrary, in a case where the calculated correlation coefficients do not match, the detection unit 122 detects abnormality of the sensor. Note that the detection unit 122 may not detect abnormality of the sensor from generation of the shock to the end thereof, i.e., while the above-mentioned shock is being generated.

Note that, in the above-mentioned description, the example where acceleration exceeds the upper limit of the second measurable range has been described. However, essentially similar processing is performed also in a case where acceleration exceeds the lower limit of the second measurable range.

(Storage Unit)

The storage unit 124 stores information for use in processing performed in the information processing apparatus 100-1. Specifically, the storage unit 124 stores measurement information received by the communication unit 120 in time series. Further, the storage unit 124 stores image information regarding an image that the display unit 128 is caused to display. Note that the image information may be stored in advance or may be additionally acquired via the communication unit 120.

(Display Control Unit)

The display control unit 126 controls processing of the display unit 128. Specifically, the display control unit 126 controls output processing for notification regarding detected abnormality. The notification regarding abnormality includes display for the user, and the display control unit 126 determines image information regarding the display. For example, the display control unit 126 selects, from the storage unit 124, image information regarding an image showing a method for solving abnormality detected by the detection unit 122 to the user and provides the selected image information to the display unit 128. Note that the display control unit 126 may generate new image information on the basis of the image information stored on the storage unit 124.

(Display Unit)

The display unit 128 displays an image on the basis of image information as an output unit. Specifically, the display unit 128 displays an image regarding image information provided from the display control unit 126 for the user.

<1-3. Processing of Apparatus>

Figure 8:
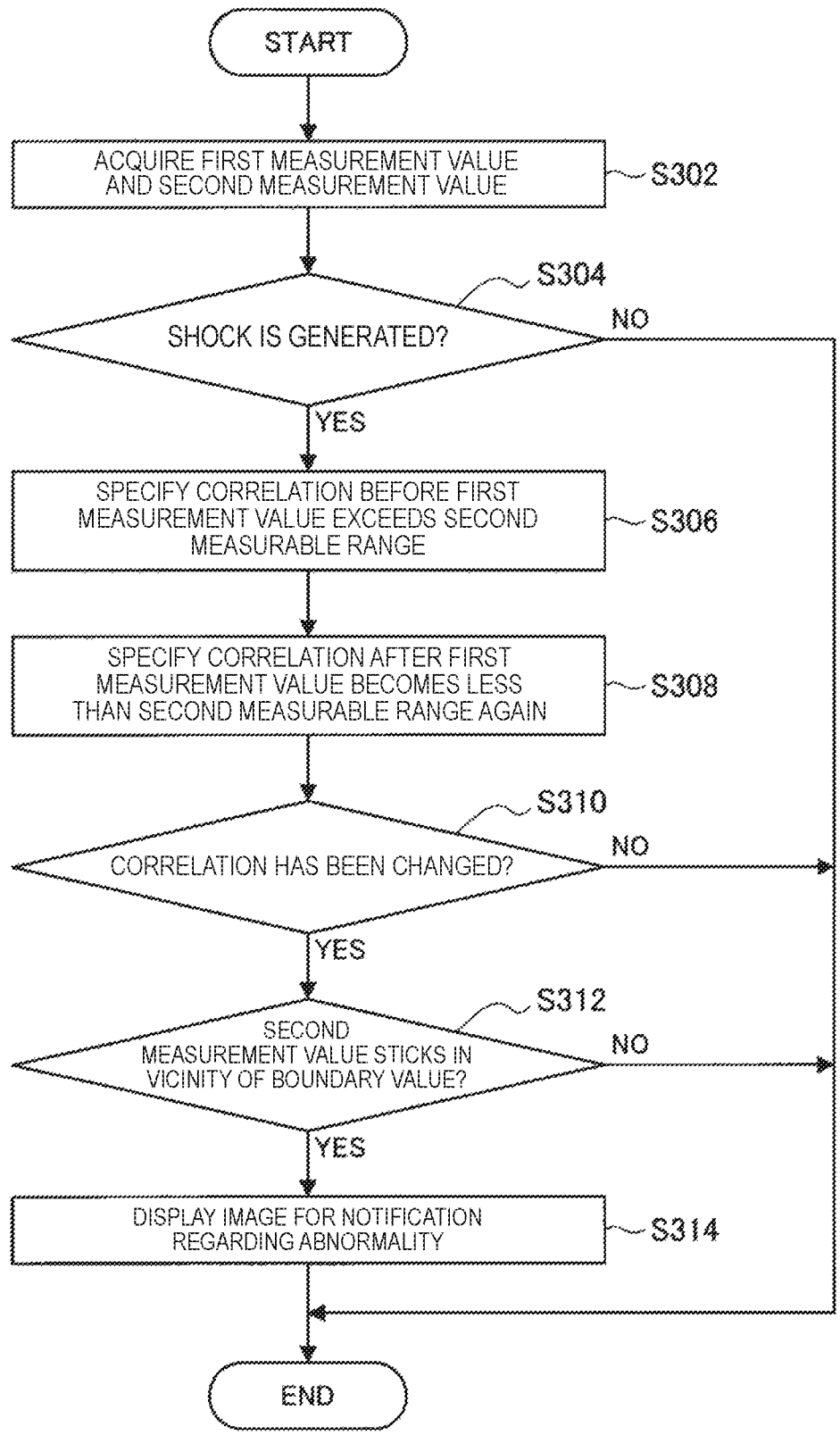
FIG. 8 is a flowchart conceptually showing processing of the information processing apparatus according to this embodiment.

Next, processing of the information processing apparatus 100-1 according to the present embodiment will be described with reference to FIG. 8. FIG. 8 is a flowchart conceptually showing processing of the information processing apparatus 100-1 according to the present embodiment.

The information processing apparatus 100-1 acquires a first measurement value and a second measurement value (Step S302). Specifically, the communication unit 120 receives a first measurement value and a second measurement value from the first acceleration sensor 200A and the second acceleration sensor 200B, respectively. Then, the received measurement values are stored on the storage unit 124.

Then, the information processing apparatus 100-1 determines whether or not a shock has been generated (Step S304). Specifically, the detection unit 122 determines whether or not a shock has been generated in the acceleration sensor 200 on the basis of time-series measurement values stored on the storage unit 124. Note that notification of generation of a shock may be given from an external device.

When it is determined that a shock has been generated, the information processing apparatus 100-1 specifies the correlation before the first measurement value exceeds the second measurable range (Step S306). Specifically, when it is determined that a shock has been generated, the detection unit 122 calculates a correlation coefficient between the first measurement value and the second measurement value in a predetermined period of time before the shock is generated, i.e., until the first measurement value reaches the low_acc_max.

Then, the information processing apparatus 100-1 specifies the correlation after the first measurement value becomes less than the second measurable range again (Step S308). Specifically, the detection unit 122 calculates a correlation coefficient between the first measurement value and the second measurement value in a predetermined period of time after the shock ends, i.e., after the first measurement value exceeds the low_acc_max and then becomes less than the low_acc_max again.

Then, the information processing apparatus 100-1 determines whether or not the correlation has been changed (Step S310). Specifically, the detection unit 122 determines whether or not the correlation coefficient before the shock is generated matches with the correlation coefficient after the shock ends or whether or not a difference between those correlation coefficients falls within a predetermined range.

When it is determined that the correlation has been changed, the information processing apparatus 100-1 determines whether or not the second measurement value sticks in the vicinity of a boundary value of the second measurable range (Step S312). Specifically, when it is determined that the correlation coefficients do not match or the difference between the correlation coefficients does not fall within the predetermined range, the detection unit 122 determines whether or not the second measurement value sticks in the vicinity of the upper limit or lower limit of the second measurable range.

When it is determined that the second measurement value sticks in the vicinity of the boundary value of the second measurable range, the information processing apparatus 100-1 displays an image for notification regarding abnormality (Step S312). Specifically, when it is determined that the second measurement value sticks in the vicinity of the upper limit or lower limit of the second measurable range, the display control unit 126 selects image information regarding an image for notifying the user of abnormality. Then, the display control unit 126 causes the display unit 128 to display the selected image.

<1-4. Conclusion of First Embodiment>

As described above, according to the first embodiment of the present disclosure, the information processing apparatus 100-1 obtains a first value (first measurement value) obtained by measurement in the first measurement unit (first acceleration sensor 200A) and a second value (second measurement value) obtained by measurement in the second measurement unit (second acceleration sensor 200B) whose dynamic range regarding measurement is the second dynamic range different from the first dynamic range of the first measurement unit. In addition, the information processing apparatus 100-1 detects abnormality of the first measurement value or the second measurement value on the basis of a change in a correlation between the first measurement value and the second measurement value. Herein, the change in the correlation means presence/absence of a change between the first measurement value and the second measurement value or a difference in a degree of the change. Therefore, in a case where the correlation is changed, a possibility that abnormality has occurred in the first measurement value or the second measurement value is increased. Further, because the first and second measurement values obtained from the acceleration sensors 200 are used for detection processing of abnormality, it is possible to use the existing acceleration sensors 200 as they are. Therefore, it is possible to improve accuracy of detecting abnormality of the acceleration sensors 200 without changing the configurations of the acceleration sensors 200.

Further, the change in the correlation includes a change between the correlation before a shock applied to the first acceleration sensor 200A and the second acceleration sensor 200B is generated and the correlation after the shock ends. Therefore, even in a case where acceleration exceeding a measurable range of the acceleration sensor 200 having a lower dynamic range is generated due to the shock and the correlation between the first and second measurement values is changed, it is possible to detect no abnormality while the acceleration is being generated. Therefore, detected abnormalities are reduced, and thus it is possible to reduce time, effort, or the like to solve the abnormality.

Further, the first dynamic range is higher than the second dynamic range, and the change in the correlation includes a change between the correlation before the first measurement value exceeds the measurable range (second measurable range) of the second acceleration sensor 200B and the correlation after the first measurement value falls within the second measurable range again. Therefore, a monitor section of the change in the correlation is determined on the basis of the first measurement value that does not easily reach a limit of the measurable range (is not easily saturated), as compared to the second measurement value, and thus accuracy of the monitor section is improved. This makes it possible to detect occurrence of abnormality of the second measurement value more accurately.

Further, when the second value is fixed in the vicinity of a predetermined value after the first value falls within the measurable range of the second measurement unit again, the information processing apparatus 100-1 detects the abnormality. Therefore, it is possible to reduce detection patterns of abnormality to sticking in the vicinity of the predetermined value. This makes it possible to reduce detection processing time, a processing load, and the like.

Further, the predetermined value includes a boundary value of the measurable range of the second measurement unit. Herein, it is found that, in a case where acceleration exceeding the second measurable range is generated, there occurs a phenomenon in which the second measurement value sticks in the vicinity of the boundary value of the second measurable range. Therefore, detection patterns are reduced in terms of the value, and thus it is possible to further reduce the detection processing time, the processing load, and the like.

Further, the information processing apparatus 100-1 performs the detection processing of the abnormality in response to generation of the shock. Therefore, it is possible to reduce frequency of the detection processing, as compared to a case where the detection processing is performed every time when a measurement value is acquired. Thus, the detection processing is made efficient. This makes it possible to reduce a processing load and power consumption regarding the detection processing.

Further, the change in the correlation includes presence/absence of the correlation or a change in a degree of the correlation. Herein, it is considered that, when the measurement value sticks as described above, there is substantially no correlation between the measurement values. Therefore, there is no problem even in a case where the abnormality is detected on the basis of presence/absence of the correlation. Further, with this, it is possible to simplify the detection processing of the abnormality. Further, in another example, it is also considered that the measurement value does not stick but there is a difference between degrees of changes in the measurement values. In that case, although it is difficult to detect the abnormality on the basis of presence/absence of the correlation, it is possible to detect the abnormality on the basis of the change in the degree of the correlation.

Further, the information processing apparatus 100-1 further includes the output unit that performs output for notification regarding the abnormality. Therefore, notification that the abnormality has been detected is given to the outside. This makes it possible to prompt an external device or the user to solve the abnormality. Note that the display unit 128 operates as the output unit in the present embodiment. However, for example, the communication unit 120 may transmit information regarding the detected abnormality to the external device as the output unit, or the information regarding the abnormality may be provided to another apparatus or module included in an apparatus in which the information processing apparatus 100-1 is incorporated.

Further, the notification includes notification of a method for solving the abnormality. Therefore, in a case where a method for solving the detected abnormality is specified, a possibility of solving the abnormality can be improved by giving notification of the method.

Further, the output includes display of the notification for the user. Therefore, visual information is presented to the user, and thus it is possible to cause the user to easily understand the notification. Note that, although the example where display is used as output for the user has been described in the present embodiment, the output for the user may be another output such as audio output.

Note that the example where the detection processing of abnormality of the measurement value, i.e., abnormality of the acceleration sensor 200 is performed in the information processing apparatus 100-1 including the display control unit 126 and the display unit 128 has been described in the present embodiment. However, the acceleration sensor 200 may be a sensor module including the detection unit 122. In that case, the abnormality detection processing is performed in the acceleration sensor 200, and a detection result is transmitted to the information processing apparatus 100-1 via communication. Then, the display control unit 126 controls display of the display unit 128 on the basis of the detection result.

2. Second Embodiment (Example of Angular Velocity Sensor)

Hereinabove, the first embodiment of the present disclosure has been described. Next, the second embodiment of the present disclosure will be described. In the second embodiment, there will be described a mechanism that detects abnormality occurring in a sensor and notifies a user of the abnormality by using angular velocity sensors as an example.

<2-1. Overview>

An information processing system according to the second embodiment is different from the information processing system according to the first embodiment in the following two points: the type of sensors is different; and the sensors are provided in the information processing apparatus 100-2. Specifically, the sensors in the information processing system according to the present embodiment are angular velocity sensors 118, and the angular velocity sensors 118 are provided in the information processing apparatus 100-2. The two angular velocity sensors, i.e., a first angular velocity sensor 118A and a second angular velocity sensor 118B, as well as the acceleration sensors 200 in the first embodiment, are provided, and a dynamic range of the first angular velocity sensor 118A is higher than that of the second angular velocity sensor 118B. Each of the angular velocity sensors 118 measures an angular velocity and generates measurement information including a measurement value indicating the measured angular velocity. Then, the generated measurement information is provided to the detection unit 122 and the like. As in the first embodiment, the information processing apparatus 100-2 including the angular velocity sensors 118 is used in sport and the like.

Figure 9:
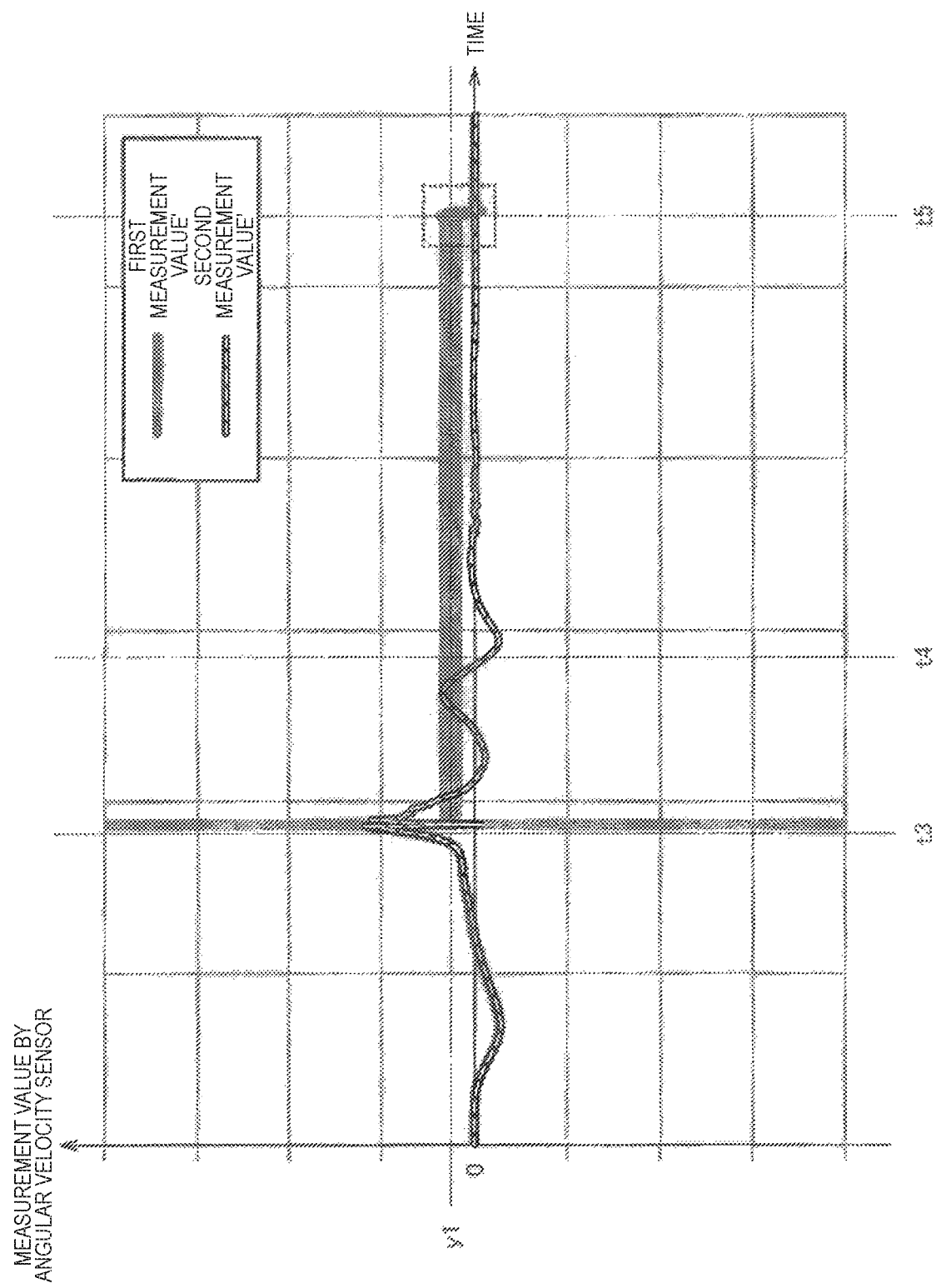
FIG. 9 is a graph showing an example of a sticking phenomenon of a measurement value of a first angular velocity sensor caused by a shock.
Figure 10:
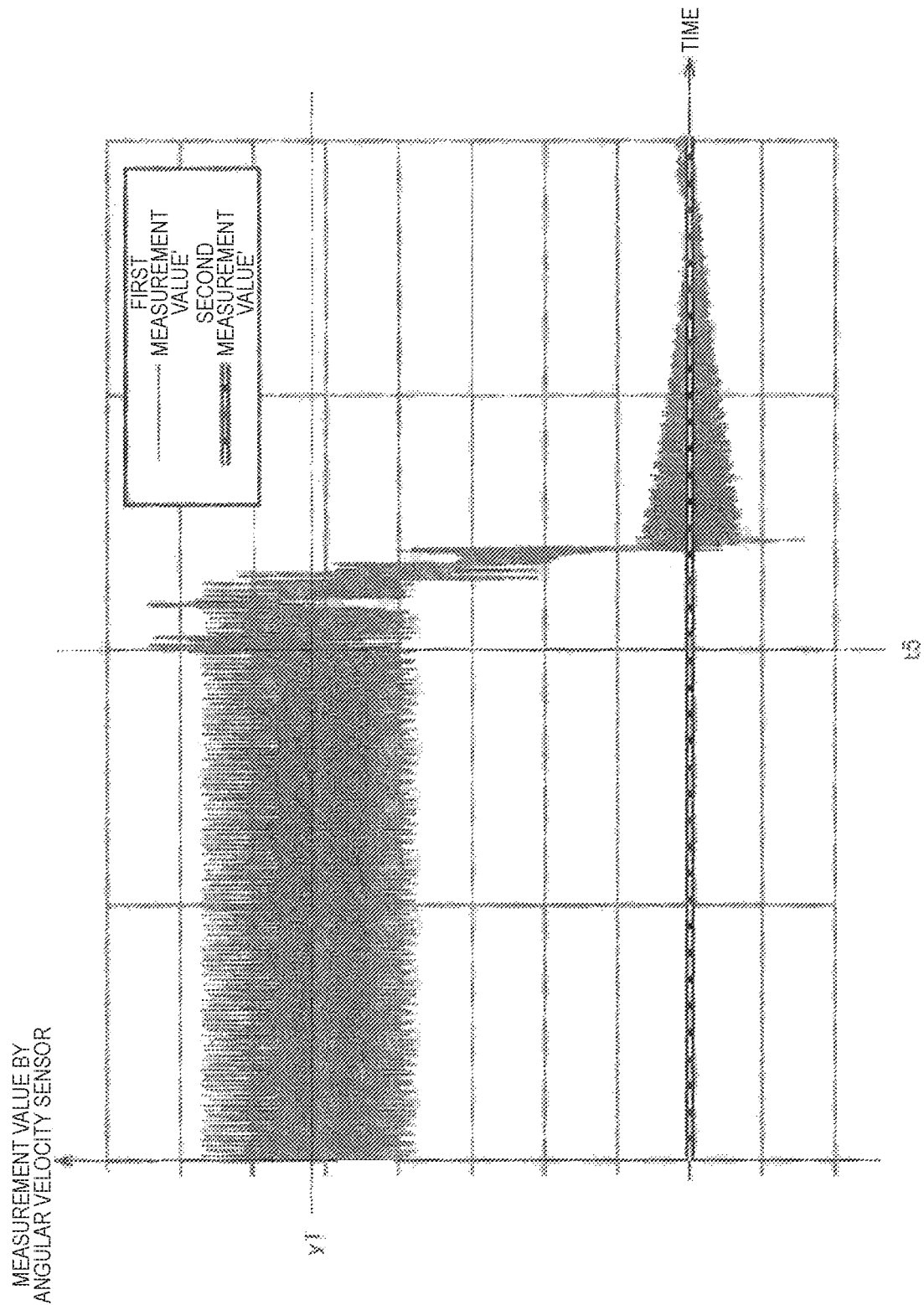
FIG. 10 is an enlarged view of a section in which the sticking phenomenon in FIG. 9 is solved.

Herein, also in a case where the angular velocity sensors are used, abnormality occurs in the angular velocity sensors due to a shock in some cases. Specifically, measurement information of the second angular velocity sensor 118B having a relatively high dynamic range sticks in the vicinity of an arbitrary value after a shock is generated, and sticking of the measurement information continues after the shock ends. Further, a sticking phenomenon of the angular velocity sensor 118 caused by the shock will be described in detail with reference to FIGS. 9 and 10. FIG. 9 is a graph showing an example of a sticking phenomenon of a measurement value of the first angular velocity sensor 118A caused by a shock, and FIG. 10 is an enlarged view of a section in which the sticking phenomenon in FIG. 9 is solved.

First, a case where no abnormality occurs in the sensor will be described. For example, a measurement value of the first angular velocity sensor 118A (hereinafter, also referred to as "first measurement information'" or "first measurement value'") (bold line) is sharply and vertically changed in response to generation of a shock in the vicinity of a time t3 illustrated in FIG. 9. At this time, a measurement value of the second angular velocity sensor 118B (hereinafter, also referred to as "second measurement information'" or "second measurement value'") (broken line) is changed along with the first measurement value' before the shock is generated and is separated from the first measurement value' when the shock is generated because the angular velocity exceeds a measurable range of the second angular velocity sensor 118B (hereinafter, also referred to as "second measurable range'"). Then, when the shock ends, the second measurement value' starts to be changed along with the first measurement value' again. This is a phenomenon occurring because the dynamic range of the second angular velocity sensor 118B is low, and therefore, generally, this phenomenon is not considered to be abnormality of the sensor.

On the contrary, in a case where abnormality occurs in the sensor, abnormality also occurs in measurement information'. For example, the second measurement value' is changed in accordance with the angular velocity generated after the shock ends, whereas the first measurement value' sticks in the vicinity of an arbitrary value y1 illustrated in FIG. 9 in some cases. Note that the first measurement value' can be changed slightly up and down around the arbitrary value y1 as illustrated in FIGS. 9 and 10.

Note that a measurement-value sticking phenomenon according to the present embodiment is solved when time elapses in some cases, which is different from the phenomenon according to the first embodiment. For example, when a time t5 illustrated in FIG. 10 comes after the measurement value' sticks, the first measurement value' starts to be changed and then is changed to match with the second measurement value', i.e., an actual angular velocity.

However, it is uncertain whether or not the measurement-value sticking phenomenon is solved when time elapses, and a length of waiting time taken for solution is also uncertain. Further, the first measurement value' having a relatively high dynamic range sticks to an arbitrary value, which is different from a case of the first embodiment, and therefore it is difficult to detect abnormality by using the configuration of the information processing apparatus 100-1 as it is.

In view of this, the present embodiment proposes an information processing system capable of detecting abnormality of the first measurement value' or the second measurement value' without using a relationship between the first measurement value' and the second measurable range' used to determine detection of abnormality in the first embodiment. Hereinafter, constituent members of the information processing system will be described in detail.

<2-2. Configuration of Apparatus>

Next, a configuration of the information processing apparatus 100-2 according to the present embodiment will be described. Note that description of a configuration substantially the same as that of the first embodiment will be omitted.

(Physical Configuration of Information Processing Apparatus)

Figure 11:
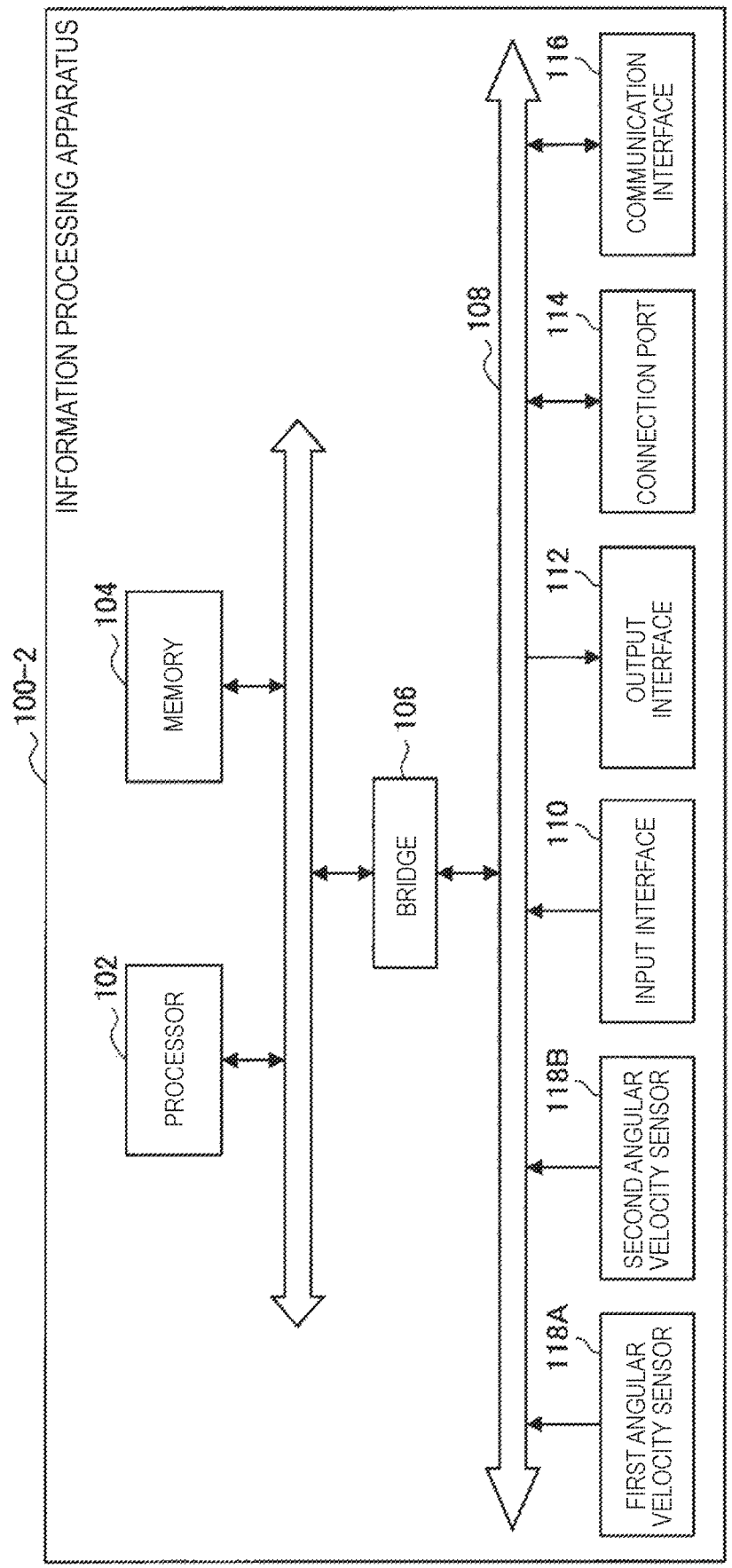
FIG. 11 is a block diagram illustrating a schematic physical configuration example of an information processing apparatus according to a second embodiment of the present disclosure.

First, a physical configuration of the information processing apparatus 100-2 will be described with reference to FIG. 11. FIG. 11 is a block diagram illustrating a schematic physical configuration example of the information processing apparatus 100-2 according to the present embodiment.

As illustrated in FIG. 11, the information processing apparatus 100-2 includes not only the processor 102, the memory 104, the bridge 106, the bus 108, the input interface 110, the output interface 112, the connection port 114, and the communication interface 116 but also the first angular velocity sensor 118A and the second angular velocity sensor 118B.

(Angular Velocity Sensor)

The angular velocity sensors 118 (i.e., the first angular velocity sensor 118A and the second angular velocity sensor 118B) measure angular velocities and achieve functions of a first angular velocity measurement unit 130A and a second angular velocity measurement unit 130B described below included in the information processing apparatus 100-2. Note that each of the angular velocity sensors 118 may be a sensor module including a processor that processes the measured angular velocity.

(Logical Configuration of Information Processing Apparatus)

Figure 12:
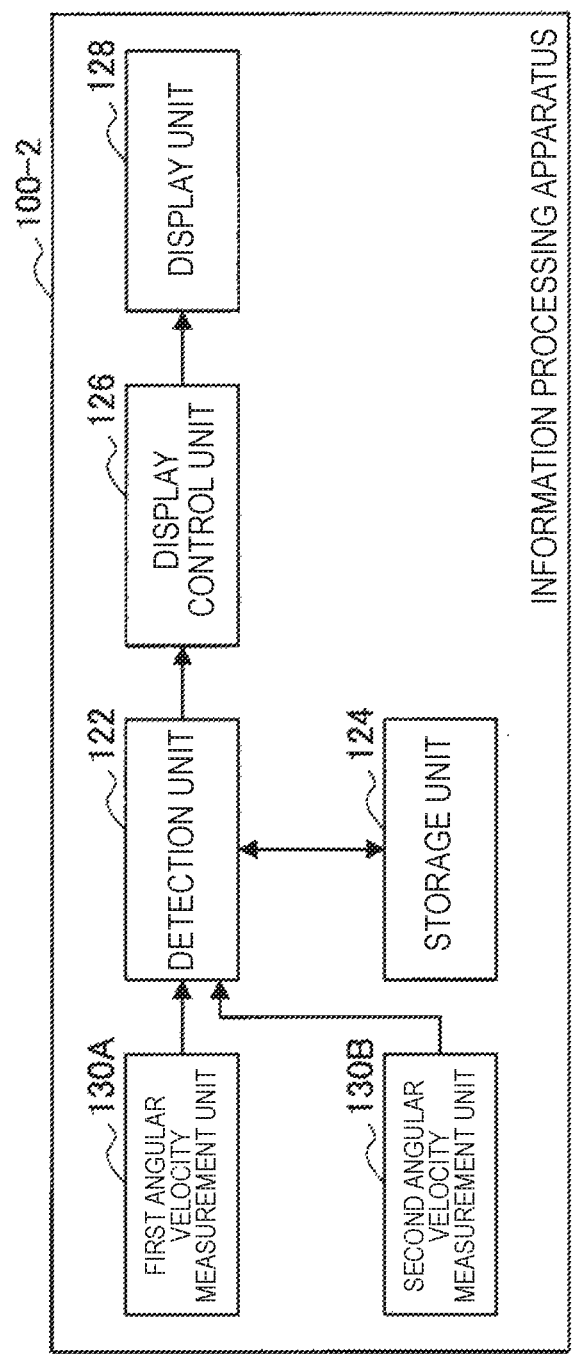
FIG. 12 is a block diagram illustrating a schematic functional configuration example of the information processing apparatus according to this embodiment.

Next, a logical configuration of the information processing apparatus 100-2 according to the present embodiment will be described with reference to FIG. 12. FIG. 12 is a block diagram illustrating a schematic functional configuration example of the information processing apparatus 100-2 according to the present embodiment.

As illustrated in FIG. 12, the information processing apparatus 100-2 includes not only the detection unit 122, the storage unit 124, the display control unit 126, and the display unit 128 but also the first angular velocity measurement unit 130A and the second angular velocity measurement unit 130B. Note that the communication unit 120 may be provided as in the first embodiment.

(Angular Velocity Measurement Unit)

Each angular velocity measurement unit 130 measures an angular velocity of the information processing apparatus 100-2. Specifically, the angular velocity measurement unit 130 measures an angular velocity and generates measurement information' including a measurement value' indicating the measured angular velocity. The generated measurement information' is provided to the detection unit 122. Note that the first angular velocity measurement unit 130A serving as the first measurement unit has a dynamic range higher than that of the second angular velocity measurement unit 130B serving as the second measurement unit.

(Detection Unit)

Figure 13:
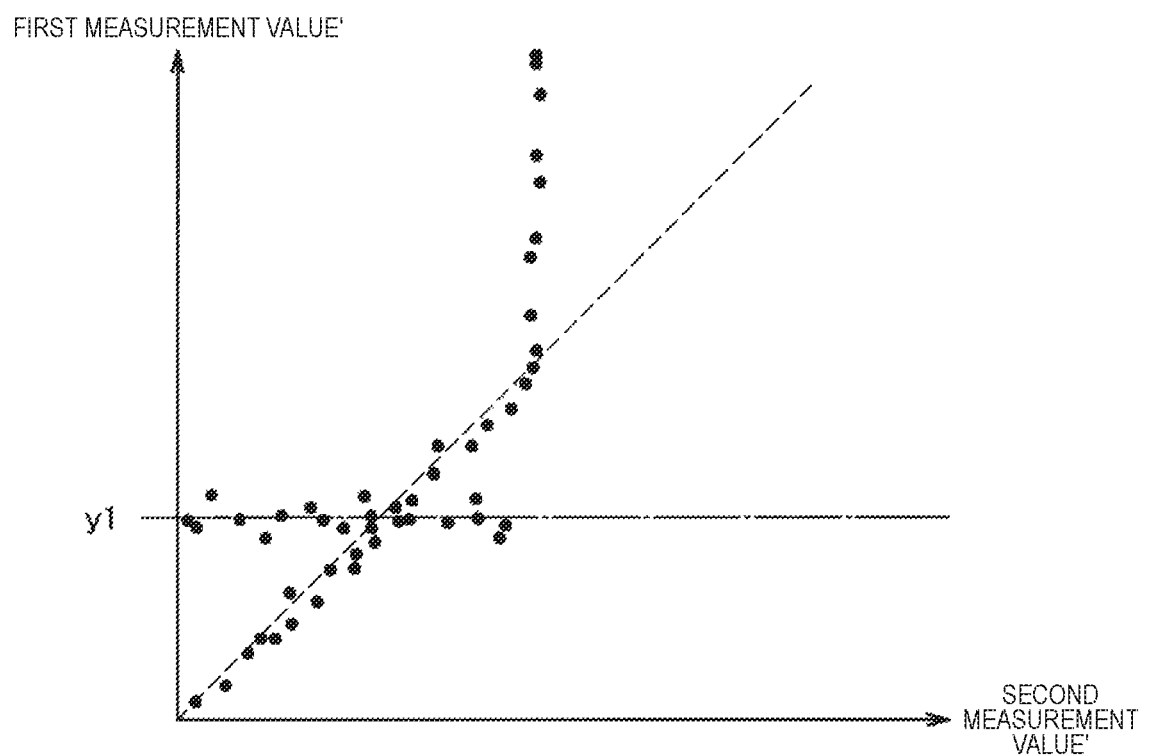
FIG. 13 is a graph showing an example of a correlation between a first measurement value' and a second measurement value' obtained in a case where abnormality occurs in the first angular velocity sensor.

The detection unit 122 detects abnormality of the measurement information' provided from the angular velocity measurement unit 130 (i.e., abnormality of the angular velocity sensor 118). Specifically, the detection unit 122 detects abnormality of the first or second measurement information' on the basis of a change in a correlation between the first measurement information' obtained by measurement in the first angular velocity measurement unit 130A serving as a first value and the second measurement information' obtained by measurement in the second angular velocity measurement unit 130B serving as a second value. Further, processing of the detection unit 122 in the present embodiment will be described in detail with reference to FIG. 13. FIG. 13 is a graph showing an example of the correlation between the first measurement value' and the second measurement value' obtained in a case where abnormality occurs in the first angular velocity sensor 118A.

First, the detection unit 122 determines whether or not a shock has been generated on the basis of measurement information'. For example, in a case where an inclination of a change in a measurement value' in the vicinity of the time t3 illustrated in FIG. 9 is equal to or larger than a threshold, the detection unit 122 determines that a shock has been generated.

In a case where it is determined that a shock has been generated, the detection unit 122 specifies the correlation before the shock is generated and the correlation after predetermined time elapses from generation of the shock. For example, the detection unit 122 calculates a correlation coefficient in a predetermined period of time before the shock is generated and a correlation coefficient in a predetermined period of time after the predetermined time elapses from generation of the shock. Note that, in a case where it is determined that the shock ends, instead of the correlation after the predetermined time elapses from generation of the shock, the correlation after the same or another predetermined time elapses from the end of the shock may be used.

Then, the detection unit 122 determines whether or not the correlation after the predetermined time elapses from generation of the shock has been changed. Specifically, the detection unit 122 determines whether or not the correlation coefficient before the shock is generated matches with the correlation coefficient after the predetermined time elapses from generation of the shock or whether or not those correlation coefficients fall within a predetermined range.

Specifically, first, as illustrated in FIG. 13, the correlation in the predetermined period of time before the shock is generated, i.e., before the correlation has a relationship substantially in parallel to an axis of the first measurement value' has a nearly linear relationship. Therefore, a positive correlation coefficient is calculated in this period of time.

Further, the second measurement value' does not follow a change in the first measurement value' while the shock is being generated, and therefore, as illustrated in FIG. 13, there is no correlation between the measurement values', and the correlation has a relationship in parallel to the axis of the first measurement value'. Therefore, a calculated correlation coefficient has 0 or a value close to 0 in this period of time.

Further, for example, at a time t4 illustrated in FIG. 9 after the predetermined time elapses from generation of the shock, the second measurement value' converges to 0 while being vertically changed along the generated angular velocity, whereas the first measurement value' sticks in the vicinity of the arbitrary value y1. Therefore, there is no correlation, as in the period in which the shock is generated. Note that the first measurement value' sticks in this case, and therefore the correlation is a relationship in parallel to the second measurement value'. A correlation coefficient of 0 or close to 0 is calculated in this period of time. Further, in the above-mentioned description, the example where the first measurement value' sticks in the vicinity of an arbitrary value has been described. However, the first measurement value' may stick in the vicinity of a fixed value instead of the arbitrary value.

Therefore, in this case, the detection unit 122 determines that the correlation coefficient before the shock is generated does not match with the correlation coefficient after the predetermined time elapses from generation of the shock.

Then, in a case where it is determined that the correlation after the predetermined time elapses from generation of the shock has been changed from the correlation before the shock is generated, the detection unit 122 detects abnormality of the sensor.

<2-3. Processing of Apparatus>

Figure 14:
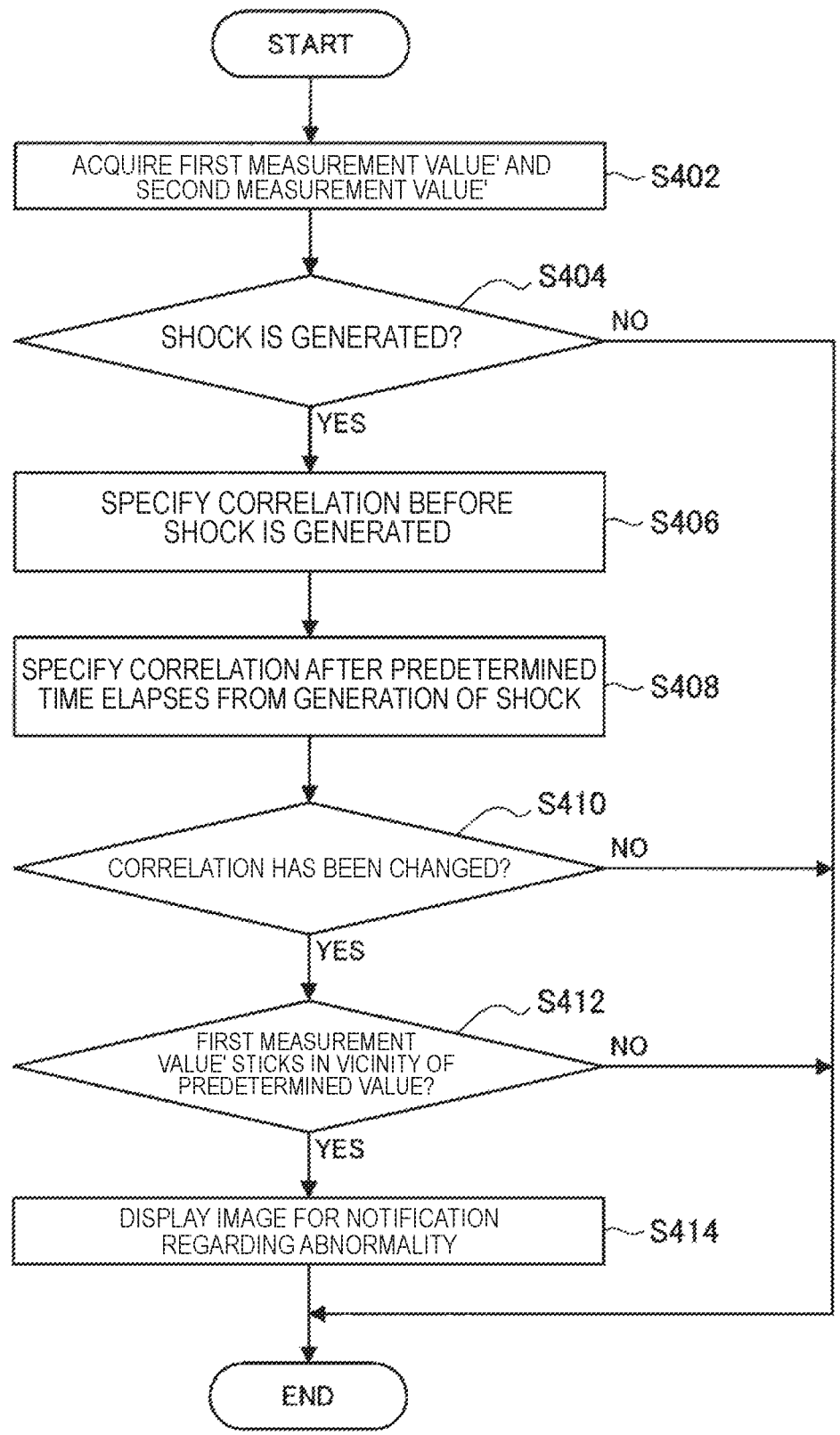
FIG. 14 is a flowchart conceptually showing processing of the information processing apparatus according to this embodiment.

Next, processing of the information processing apparatus 100-2 according to the present embodiment will be described with reference to FIG. 14. FIG. 14 is a flowchart conceptually showing processing of the information processing apparatus 100-2 according to the present embodiment. Note that description of processing that is substantially the same as the processing according to the first embodiment will be omitted.

The information processing apparatus 100-2 acquires a first measurement value' and a second measurement value' (Step S402) and determines whether or not a shock has been generated on the basis of the acquired measurement values' (Step S404).

When it is determined that a shock has been generated, the information processing apparatus 100-2 specifies the correlation before the shock is generated (Step S406) and specifies the correlation after a predetermined time elapses from generation of the shock (Step S408).

Then, the information processing apparatus 100-1 determines whether or not the correlation has been changed (Step S410). Specifically, the detection unit 122 determines whether or not a correlation coefficient before the shock is generated matches with a correlation coefficient after the predetermined time elapses from generation of the shock or whether or not a difference between those correlation coefficients falls within a predetermined range.

When it is determined that the correlation has been changed, the information processing apparatus 100-2 determines whether or not the first measurement value' sticks in the vicinity of a predetermined value (Step S412). Specifically, when it is determined that the calculated correlation coefficients do not match, the detection unit 122 determines whether or not the first measurement value' sticks in the vicinity of an arbitrary value.

When it is determined that the first measurement value' sticks in the vicinity of the predetermined value, the information processing apparatus 100-2 displays an image for notification regarding abnormality (Step S414).

<2-4. Conclusion of Second Embodiment>

As described above, according to the second embodiment of the present disclosure, the information processing apparatus 100-2 detects the abnormality on the basis of a change between the correlation before the shock is generated and the correlation after the predetermined time elapses from generation of the shock. Therefore, it is possible to determine the end of the shock without using a relationship between a measurement value' and a measurable range' as in the first embodiment. Therefore, more abnormalities can be set as targets to be detected.

Further, the information processing apparatus 100-2 detects the abnormality when the first value is fixed in the vicinity of a predetermined value after the predetermined time elapses from generation of the shock. Therefore, it is possible to reduce detection patterns of abnormality to sticking in the vicinity of the predetermined value. This makes it possible to reduce detection processing time, a processing load, and the like.

Further, the information processing apparatus 100-2 further includes the first measurement unit and the second measurement unit. Recently, information processing apparatuses such as portable terminals including various sensors have been increased, and a similar phenomenon may occur in the sensors included in such information processing apparatuses. Regarding this, according to the present configuration, it is possible to obtain an effect regarding detection of abnormality also in the information processing apparatuses including the sensors.

3. Conclusion

Hereinabove, according to the first embodiment of the present disclosure, it is possible to improve accuracy of detecting abnormality of the acceleration sensors 200 without changing the configurations of the acceleration sensors 200.

Further, according to the second embodiment of the present disclosure, it is possible to determine the end of the shock without using a relationship between a measurement value' and a measurable range' as in the first embodiment. Therefore, more abnormalities can be set as targets to be detected.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, in the above-mentioned embodiments, the examples where measurement information is a measurement value indicating a degree of a phenomenon of a target to be measured such as acceleration or an angular velocity have been described. However, the present technology is not limited to such examples. For example, the measurement information may be other information that is changed in accordance with a measurement result such as an oscillation frequency or frequency obtained in measurement.

Further, in the above-mentioned embodiments, the examples where the information processing system is applied to sport have been described. However, the information processing system may be applied to other fields. For example, the information processing system may be applied to construction work, farm work, or the like.

Further, the effects described in this specification are merely illustrative or exemplified effects, and are not limitative. That is, with or in the place of the above effects, the technology according to the present disclosure may achieve other effects that are clear to those skilled in the art from the description of this specification.

Further, steps illustrated in the flowcharts of the above embodiment include not only processes which are chronologically performed in accordance with the described order but also processes which are not necessarily chronologically performed but performed in parallel or individually as well. Further, it is needless to say that even in steps which are processed chronologically, the order can be appropriately changed depending on circumstances.

Further, it is possible to create a computer program causing hardware installed in the information processing apparatus 100 to perform functions equivalent to the logical components of the information processing apparatus 100. A storage medium storing the computer program may also be provided.

Additionally, the present technology may also be configured as below.

(1)

An information processing apparatus including:

an acquisition unit configured to obtain a first value obtained by measurement in a first measurement unit and a second value obtained by measurement in a second measurement unit whose dynamic range regarding measurement is a second dynamic range different from a first dynamic range of the first measurement unit; and a detection unit configured to detect abnormality of the first value or the second value on a basis of a change in a correlation between the first value and the second value.

(2)

The information processing apparatus according to (1), in which the change in the correlation includes a change between the correlation before a shock applied to the first measurement unit and the second measurement unit is generated and the correlation after the shock ends.

(3)

The information processing apparatus according to (2), in which the first dynamic range is higher than the second dynamic range, and the change in the correlation includes a change between the correlation before the first value exceeds a measurable range of the second measurement unit and the correlation after the first value falls within the measurable range of the second measurement unit again.

(4)

The information processing apparatus according to (3), in which when the second value is fixed in a vicinity of a predetermined value after the first value falls within the measurable range of the second measurement unit again, the detection unit detects the abnormality.

(5)

The information processing apparatus according to (4), in which the predetermined value includes a boundary value of the measurable range of the second measurement unit.

(6)

The information processing apparatus according to any one of (2) to (5), in which the end of the shock includes elapse of predetermined time from generation of the shock.

(7)

The information processing apparatus according to (6), in which the first dynamic range is higher than the second dynamic range, and when the first value is fixed in a vicinity of a predetermined value after the predetermined time elapses from generation of the shock, the detection unit detects the abnormality.

(8)

The information processing apparatus according to any one of (2) to (7), in which
the detection unit performs detection processing of the abnormality in response to generation of the shock.

(9)

The information processing apparatus according to any one of (2) to (8), in which
the change in the correlation includes presence/absence of the correlation or a change in a degree of the correlation.

(10)

The information processing apparatus according to any one of (2) to (9), further including:
the first measurement unit; and
the second measurement unit.

(11)

The information processing apparatus according to any one of (2) to (10), further including
an output unit configured to perform output for notification regarding the abnormality.

(12)

The information processing apparatus according to (11), in which
the notification includes notification of a method for solving the abnormality.

(13)

The information processing apparatus according to (11) or (12), in which
the output includes display of the notification for a user.

(14)

An information processing method including:
obtaining, by a processor, a first value obtained by measurement in a first measurement unit and a second value obtained by measurement in a second measurement unit whose dynamic range regarding measurement is a second dynamic range different from a first dynamic range of the first measurement unit; and
detecting abnormality of the first value or the second value on a basis of a change in a correlation between the first value and the second value.

(15)

A storage medium storing a program for causing a computer to achieve:
an acquisition function of obtaining a first value obtained by measurement in a first measurement unit and a second value obtained by measurement in a second measurement unit whose dynamic range regarding measurement is a second dynamic range different from a first dynamic range of the first measurement unit; and
a detection function of detecting abnormality of the first value or the second value on a basis of a change in a correlation between the first value and the second value.

REFERENCE SIGNS LIST 100 information processing apparatus
118 angular velocity sensor
120 communication unit
122 detection unit
124 storage unit
126 display control unit
128 display unit
130 angular velocity measurement unit
200 acceleration sensor

The invention claimed is:

1. An information processing apparatus comprising:
an acquisition unit configured to obtain a first value obtained by measurement in a first measurement unit and a second value obtained by measurement in a second measurement unit whose dynamic range regarding measurement is a second dynamic range different from a first dynamic range of the first measurement unit; and
a detection unit configured to detect abnormality of the first value or the second value based on a change in a correlation between the first value and the second value,
wherein the detection unit detects the abnormality when one of the first value or the second value is within a vicinity of a respective predetermined value after the change in the correlation,
wherein the respective predetermined value comprises an upper limit or a lower limit of a respective one of the first dynamic range or the second dynamic range,
wherein the change in the correlation is determined between the correlation before a generated shock is applied to the first measurement unit and the second measurement unit and the correlation after an end of the shock,
wherein the end of the shock used to determine the change in correlation is based on an elapse of a predetermined amount of time from generation of the shock, and
wherein the acquisition unit and the detection unit are each implemented via at least one processor.

2. The information processing apparatus according to claim 1, wherein
the first dynamic range is higher than the second dynamic range, and
the change in the correlation is further determined between the correlation before the first value exceeds the second dynamic range of the second measurement unit and the correlation after the first value falls within the second dynamic range of the second measurement unit again.

3. The information processing apparatus according to claim 2, wherein
when the second value is fixed in the vicinity of the respective predetermined value after the first value falls within the second dynamic range of the second measurement unit again, the detection unit detects the abnormality.

4. The information processing apparatus according to claim 1, wherein
the first dynamic range is higher than the second dynamic range, and
when the first value is fixed in the vicinity of the respective predetermined value after the predetermined amount of time elapses from the generation of the shock, the detection unit detects the abnormality.

5. The information processing apparatus according to claim 1, wherein
the detection unit performs detection processing of the abnormality in response to the generation of the shock.

6. The information processing apparatus according to claim 1, wherein
the change in the correlation relates to a presence, an absence, or a change in a degree of the correlation.

7. The information processing apparatus according to claim 1, further comprising:
the first measurement unit; and
the second measurement unit, wherein the first measurement unit and the second measurement unit each comprise at least one acceleration sensor.

8. The information processing apparatus according to claim 1, further comprising:
an output unit configured to perform output for notification regarding the abnormality,
wherein the output unit comprises an output interface.

9. The information processing apparatus according to claim 8, wherein
the notification includes notification of a method for solving the abnormality.

10. The information processing apparatus according to claim 8, wherein
the output includes display of the notification for a user.

11. The information processing apparatus according to claim 1,
wherein when the predetermined amount of time elapses from the generation of the shock, the detection unit detects the abnormality based on whether a correlation coefficient before the shock is generated matches with a correlation coefficient after the predetermined amount of time elapses from the generation of the shock.

12. An information processing method comprising:
obtaining, by a processor, a first value obtained by measurement in a first measurement unit and a second value obtained by measurement in a second measurement unit whose dynamic range regarding measurement is a second dynamic range different from a first dynamic range of the first measurement unit; and
detecting abnormality of the first value or the second value based on a change in a correlation between the first value and the second value,
wherein the abnormality is detected based on one of the first value or the second value being within a vicinity of a respective predetermined value after the change in the correlation,
wherein the respective predetermined value comprises an upper limit or a lower limit of a respective one of the first dynamic range or the second dynamic range,
wherein the change in the correlation is determined between the correlation before a generated shock is applied to the first measurement unit and the second measurement unit and the correlation after an end of the shock, and
wherein the end of the shock used to determine the change in correlation is based on an elapse of a predetermined amount of time from generation of the shock.

13. A non-transitory computer-readable storage medium having embodied thereon a program, which when executed by a computer causes the computer to execute a method, the method comprising:
obtaining a first value obtained by measurement in a first measurement unit and a second value obtained by measurement in a second measurement unit whose dynamic range regarding measurement is a second dynamic range different from a first dynamic range of the first measurement unit; and
detecting abnormality of the first value or the second value based on a change in a correlation between the first value and the second value,
wherein the abnormality is detected when one of the first value or the second value is within a vicinity of a respective predetermined value after the change in the correlation,
wherein the respective predetermined value comprises an upper limit or a lower limit of a respective one of the first dynamic range or the second dynamic range,
wherein the change in the correlation is determined between the correlation before a generated shock is applied to the first measurement unit and the second measurement unit and the correlation after an end of the shock, and
wherein the end of the shock used to determine the change in correlation is based on an elapse of a predetermined amount of time from generation of the shock.

* * * * *